United States Patent
Lin et al.

(10) Patent No.: US 10,792,242 B2
(45) Date of Patent: Oct. 6, 2020

(54) METHOD FOR REDUCING SKIN SAGGING AND/OR IMPROVING SKIN BRIGHTNESS BY USING GUM TRAGACANTH COMPOSITION

(71) Applicant: TCI CO., LTD, Taipei (TW)

(72) Inventors: Yung-Hsiang Lin, Taipei (TW); Tsai-Han Yao, Taipei (TW)

(73) Assignee: TCI CO., LTD., Taipei (TW)

( * ) Notice: Subject to any disclaimer, the term of this patent is extended or adjusted under 35 U.S.C. 154(b) by 547 days.

(21) Appl. No.: 15/847,729

(22) Filed: Dec. 19, 2017

(65) Prior Publication Data

US 2018/0369130 A1    Dec. 27, 2018

Related U.S. Application Data

(60) Provisional application No. 62/523,388, filed on Jun. 22, 2017.

(30) Foreign Application Priority Data

Sep. 8, 2017  (TW) .............................. 106130864 A

(51) Int. Cl.
| | | |
|---|---|---|
| A61K 36/00 | (2006.01) | |
| A61K 8/9789 | (2017.01) | |
| A61Q 19/08 | (2006.01) | |
| A61Q 19/02 | (2006.01) | |

(52) U.S. Cl.
CPC ............ *A61K 8/9789* (2017.08); *A61Q 19/02* (2013.01); *A61Q 19/08* (2013.01)

(58) Field of Classification Search
CPC ..................................................... A61K 36/00
USPC ........................................................ 424/725
See application file for complete search history.

(56) References Cited

U.S. PATENT DOCUMENTS

2009/0118378 A1    5/2009  Barbier
2017/0100326 A1    4/2017  Nogueira et al.

FOREIGN PATENT DOCUMENTS

| CN | 106420391 A | 2/2017 |
|---|---|---|
| KR | 10-2012-0119797 A | 10/2012 |
| KR | 10-2017-0005813 A | 1/2017 |

OTHER PUBLICATIONS

"Refuse to eat soil and teach you how to buy the cheapest and super effective hyaluronic acid in history!" https://www.sohu.com/a/133821283_612103, 20 pages (Apr. 13, 2017).

*Primary Examiner* — Michael V Meller
(74) *Attorney, Agent, or Firm* — Christensen, Fonder, Dardi & Herbert PLLC

(57) ABSTRACT

A method for reducing skin sagging and/or improving skin brightness is provided. The method comprises administering to a subject in need an effective amount of gum tragacanth composition, wherein the gum tragacanth composition comprises gum tragacanth and a pharmaceutically acceptable carrier and is topically administered to the skin at least once a day to achieve the effects of maintaining skin tightness and moisture and improving skin brightness.

3 Claims, 4 Drawing Sheets

METHOD FOR REDUCING SKIN SAGGING AND/OR IMPROVING SKIN BRIGHTNESS BY USING GUM TRAGACANTH COMPOSITION

CROSS REFERENCE TO RELATED APPLICATIONS

This application claims priority to U.S. Provisional Application Ser. No. 62/523,388 filed on Jun. 22, 2017, in the United States Patent and Trademark Office, and to Taiwan Patent Application No. 106130864 filed on Sep. 8, 2017, in the Taiwan Intellectual Property Office; the disclosures of which are incorporated herein in their entirety by reference.

FIELD OF THE INVENTION

The present invention relates to the uses of gum tragacanth composition. The present invention especially relates to the uses of gum tragacanth composition in reducing skin sagging and/or improving skin brightness.

BACKGROUND OF THE INVENTION

In human body, skin is the first line of defense against external damages such as ultraviolet (UV) rays, pathogens and friction, as well as against water loss. Skin, from external layer to internal layer, contains epidermis, dermis and subcutaneous tissues, wherein the dermis is primarily consisting of connective tissues. Some conditions of aging such as wrinkles, fine lines, sagging, depression, and enlarged pores may appear with age. The appearance of such aging conditions is in involved with many factors such as insufficient hyaluronic acid as well as lack of collagen and elastin in the dermis and all the aforementioned factors may reduce skin abundance and elasticity.

The commercialized approaches for alleviating the aforementioned aging conditions include injecting collagen or hyaluronic acid into the dermis directly and supplying with collagen or hyaluronic acid orally. However, it is costly to inject collagen or hyaluronic acid because the collagen or hyaluronic acid being injected into the dermis may easily be degraded by the enzymes in bodies over time, and thus, need to be applied regularly. The effect of supplying with collagen or hyaluronic acid orally is limited because the supplied collagen or hyaluronic acid would be digested into small molecules such as amino acids and monosaccharides in the gastrointestinal tract, while such small molecules can be utilized to synthesize various proteins or polysaccharides but not just collagen or hyaluronic acid.

To maintain skin elasticity and tightness and/or improve skin moisture, researchers have tried to develop a novel skin care composition for topical administration. In view of that modern people tend to use natural materials in the skin care product, there is a necessity for seeking new materials from animals and plants which are safe and against skin aging.

Gum tragacanth trees are originated from the dry areas to the east of Mediterranean sea and the plateau or desert of the southwestern and northern Asia, and a small amount of Gum tragacanth trees are distributed over southeastern Asia. The pith secretion of Gum Tragacanth tree is of white transparent and is commonly called as gum tragacanth. Some researchers have found that gum tragacanth is rich in polysaccharides and galacuronic acid and is effective in enhancing immunity, resisting upper respiratory tract infection, and alleviating diarrhea. However, the effects of gum tragacanth on skin care is still unclear.

SUMMARY OF THE INVENTION

An objective of the present invention is to provide a gum tragacanth composition for reducing skin sagging and/or improving skin brightness, wherein the gum tragacanth composition comprises gum tragacanth and a pharmaceutically acceptable carrier.

Another objective of the present invention is to provide a method for reducing skin sagging and/or improving skin brightness, comprising administering to a subject in need an effective amount of aforementioned gum tragacanth composition.

In one embodiment of the gum tragacanth composition in accordance with the present invention, the concentration of the gum tragacanth in the gum tragacanth composition is more than 1% (w/v), the pharmaceutically acceptable carrier is at least one of water, an organic solvent, and a combination thereof, and the gum tragacanth composition is topically administered to the skin of the subject at least once a day.

In one embodiment of the gum tragacanth composition in accordance with the present invention, the gum tragacanth composition for reducing skin sagging and/or improving skin brightness is administered to the subject as a medicament, a skin care product, or a cosmetic product in a form of a cream, an emulsion, a dispersing liquid, a foam, a gel, a paste, a powder, a patch, or a mask, and may further comprise at least one of hydroquinone, arbutin, salicylic acid, and alpha hydroxy acid.

The gum tragacanth composition in accordance with the present invention can significantly reduce skin sagging and improve skin moisture and brightness, and thus, can tighten skin, thereby being helpful in alleviating the conditions of skin aging such as wrinkles, sagging, depression and enlarged pores.

DESCRIPTION OF THE PREFERRED EMBODIMENTS

Figure 1:
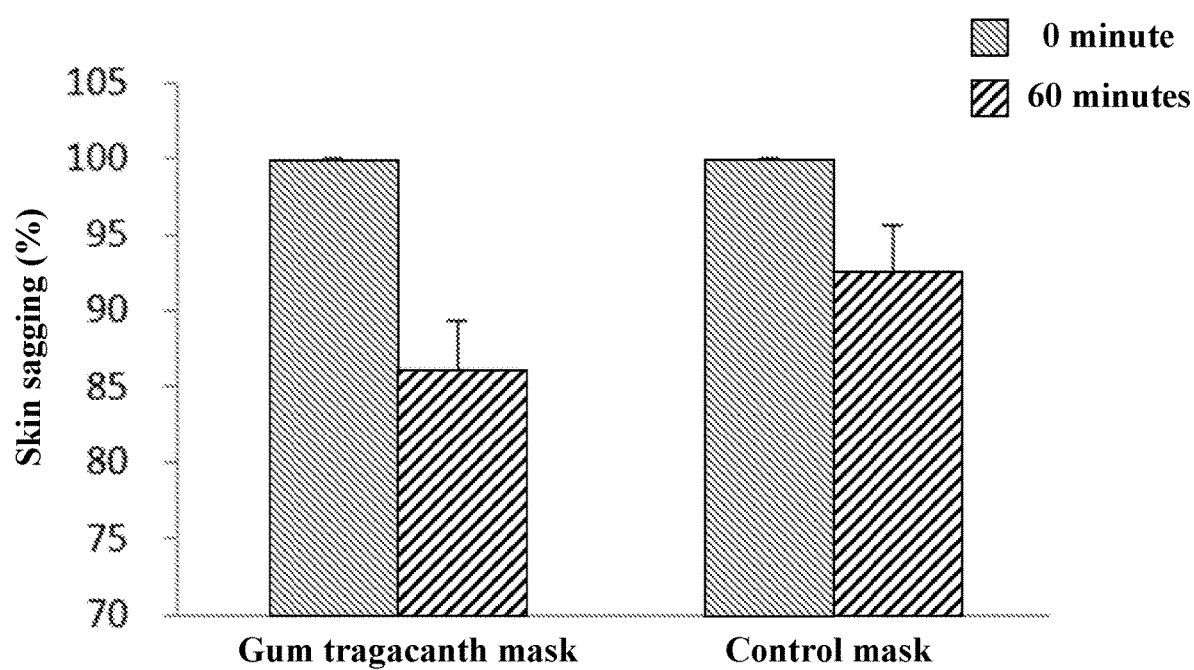
FIG. 1 shows the changes in skin sagging of the subjects, prior to and after applying a gum tragacanth mask which is filled with a 1% (w/v) gum tragacanth-containing gum tragacanth composition for 60 minutes, wherein the skin sagging prior to applying the mask is served as 100%.

The following will describe some of the embodiments of the present invention in detail. However, without departing from the spirit of the present invention, the present invention may be embodied in various embodiments and should not be limited to the embodiments described in the specification.

In addition, unless otherwise indicated herein, the expressions "a," "an," "the," or the like recited in the specification of the present invention (especially in the claims) are intended to include both the singular and plural forms. The term "an effective amount" recited in the specification refers to the amount of the composition that can at least partially reduce skin sagging and/or improve skin brightness of a subject. The term "subject" recited in this specification refers to a mammalian, including human and non-human animals. The numerical ranges recited in the specification should include all the possible combinations of numerical values between the lowest value and the highest value listed therein. In addition, the word "about", "approximately" or "almost" as used herein substantially represent values within ±20% of the stated value, preferably within ±10% and more preferably within ±5%.

The present invention relates to the uses of gum tragacanth composition in reducing skin sagging and/or improving skin brightness. In the present invention, the gum tragacanth composition comprises gum tragacanth and a pharmaceutically acceptable carrier, wherein the gum tragacanth refers to any form (e.g., gel, lump, or powder) of the pith secretion of Gum Tragacanth trees, and the pharmaceutically acceptable carrier is water, an organic solvent, or a combination thereof.

The present invention will be further illustrated in detail with specific examples as follows. However, the following examples are provided only for illustrating the present invention and the scope of the present invention is not limited thereby. The scope of the present invention will be indicated in the appended claims.

Materials and Methods
Preparation of Gum Tragacanth Composition

Gum trgacanth (habitat: Myanmar) was ground to powders. Then, 0.1-10 g gum tragacanth powder was mixed with 1-100 mL solvent evenly to provide a 0.1-10% (w/v) gum tragacanth composition (i.e., the concentration of the gum tragacanth in the composition is 0.1-10% (w/v)). The solvent could be water, an organic solvent, or a combination thereof, wherein the organic solvent could be an alcohol such as ethanol, propanediol, and glycerol.

Examination of Skin Sagging

The skin sagging was measured by a skin elasticity analyzer, Cutometer® Dual MPA 580 (purchased from Courage+Khazaka electronic GmbH, Germany). During the measurement, the probe connected to the skin elasticity analyzer was operated to contact the test area on the skin of a subject, so as to form a closed space on the skin surface and apply a negative pressure to the skin to pull the skin, and then air was introduced into the space to return the skin to a normal state. The height of the skin being pulled up was detected by the light reflection and calculated to obtain a skin sagging parameter of the test area. Since the skin sagging may be affected by some factors such as the temperature and humidity of the environment, the subjects should stay in a room with a constant temperature and a constant humidity for 10 minutes prior to being tested. In the test environment, the temperature is 20° C.±1° C., and the relative humidity is 50%±5%.

Examination of Skin Moisture

The skin moisture was measured by the moisture retention module of DermaLab® Combo ultrasonic analyzer (purchased from Cortex Technologies, Denmark). During the measurement, a probe of DermaLab® Combo ultrasonic analyzer was operated to press the test area on the skin of a subject, so as to determine the skin moisture of the test area by measuring the change of electric conductivity. Since the skin moisture may be affected by some factors such as the temperature and humidity of the environment, the subjects should stay in a room with a constant temperature and a constant humidity for 20 minutes prior to being tested. In the test environment, the temperature is 20° C.±1° C., and the relative humidity is 50%±5%.

Examination of Skin Brightness

The skin brightness was measured by a high-resolution single-lens reflex camera with two light sources (i.e., one is of full spectrum wavelength and the other is of polarized wavelength). The face skin of a subject was taken a clear photo in a closed film studio, and then the photo was analyzed by an image analyzer to determine the skin brightness.

Statistical Analysis

The significant statistical differences were determined by Student t-test of Excel.

Example 1: Effect of Gum Tragacanth Composition on Skin Tightness

To ascertain the effect of gum tragacanth composition on skin tightness, applying a gum tragacanth mask which is filled with 1% (w/v) gum tragacanth-containing gum tragacanth composition (containing placebo whose ingredients include water, SymSave® H, hexanediol, 1,3-butanediol, xanthan gum, thickening agent and triethanolamine) and a control mask (containing only placebo) to the skin of five subjects on the inner portion of arm for 20 minutes respectively, and then removing the masks and messaging the skin gently with finger pulps to enhance the absorption of mask liquid and analyzing the condition of skin at the $60^{th}$ minute counting from the time of applying the masks (the condition of skin was also analyzed prior to applying the mask). As shown in FIG. 1, after applying the mask on the skin for 60 minutes, the skin sagging of the subjects applying control mask was reduced by about 8%, and that of the subjects applying gum tragacanth mask which is filled with 1% (w/v) gum tragacanth-containing gum tragacanth composition was reduced by about 14%. These results indicate that the gum tragacanth composition can significantly improve skin tightness.

Figure 2:
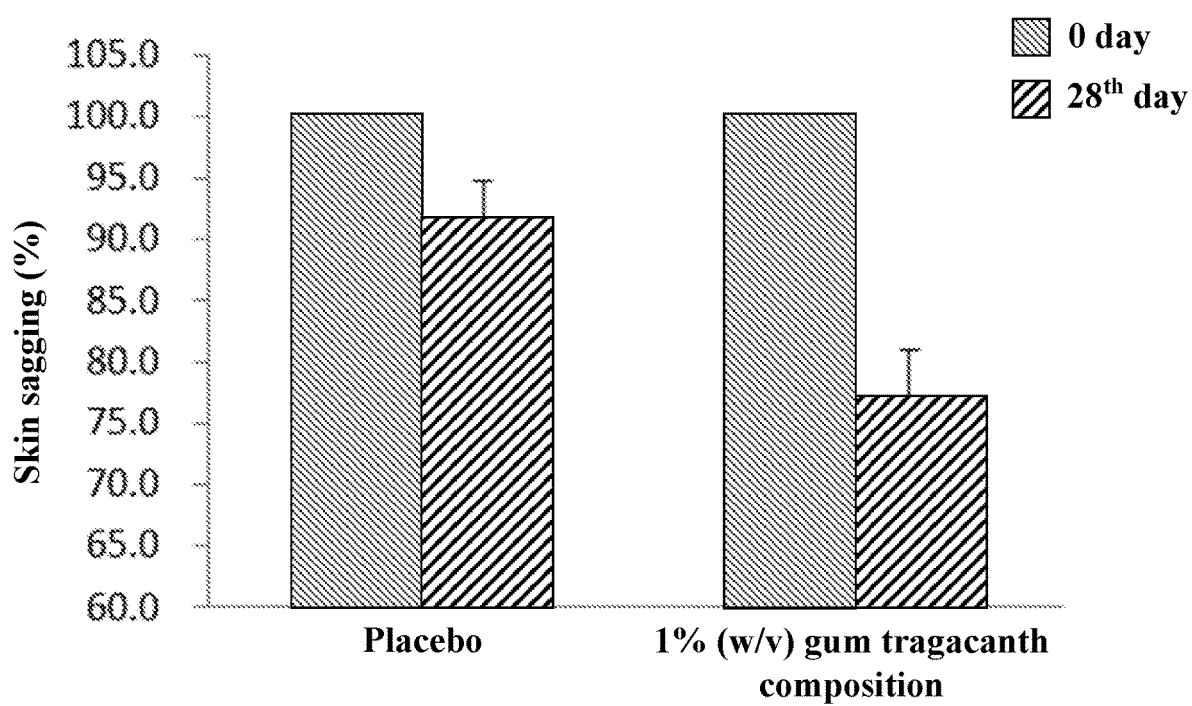
FIG. 2 shows the changes in skin sagging of the subjects, prior to and after continuously applying a 1% (w/v) gum tragacanth-containing gum tragacanth composition for 28 days, wherein the skin sagging prior to applying the composition is served as 100%.

Example 2: Long-Term Effects of Gum Tragacanth Composition on the Skin Tightness, Skin Moisture and Skin Brightness To ascertain whether the effect of the aforementioned gum tragacanth composition on skin tightness can maintain for a long time, separately applying 1% (w/v) gum tragacanth-containing gum tragacanth composition (containing placebo whose ingredients include water, SymSave® H, hexanediol, 1,3-butanediol, xanthan gum, thickening agent and triethanolamine) and placebo (ingredients include water, SymSave® H, hexanediol, 1,3-butanediol, xanthan gum, thickening agent and triethanolamine) over each half side of faces of eight subjects between 25 to 40 years old after cleaning the face in every morning and evening, then messaging the face with finger pulps to enhance the absorptions of the 1% (w/v) gum tragacanth-containing gum tragacanth composition or placebo, and analyzing the condition of skin sagging of each half side of the face at the end of the $28^{th}$ day of the experiment (the condition of skin sagging was also analyzed prior to the first application of 1% (w/v) gum tragacanth-containing gum tragacanth composition/placebo). As shown in FIG. 2, after using 1% (w/v) gum tragacanth-containing gum tragacanth composition or the placebo alone continuously for 28 days in every morning and evening, the skin sagging of the subjects using placebo alone was reduced by only about 8.2%, and that of the subjects using 1% (w/v) gum tragacanth-containing gum tragacanth composition was reduced by about 22.7%. These results indicate that gum tragacanth composition can reduce skin sagging continuously.

Figure 3:
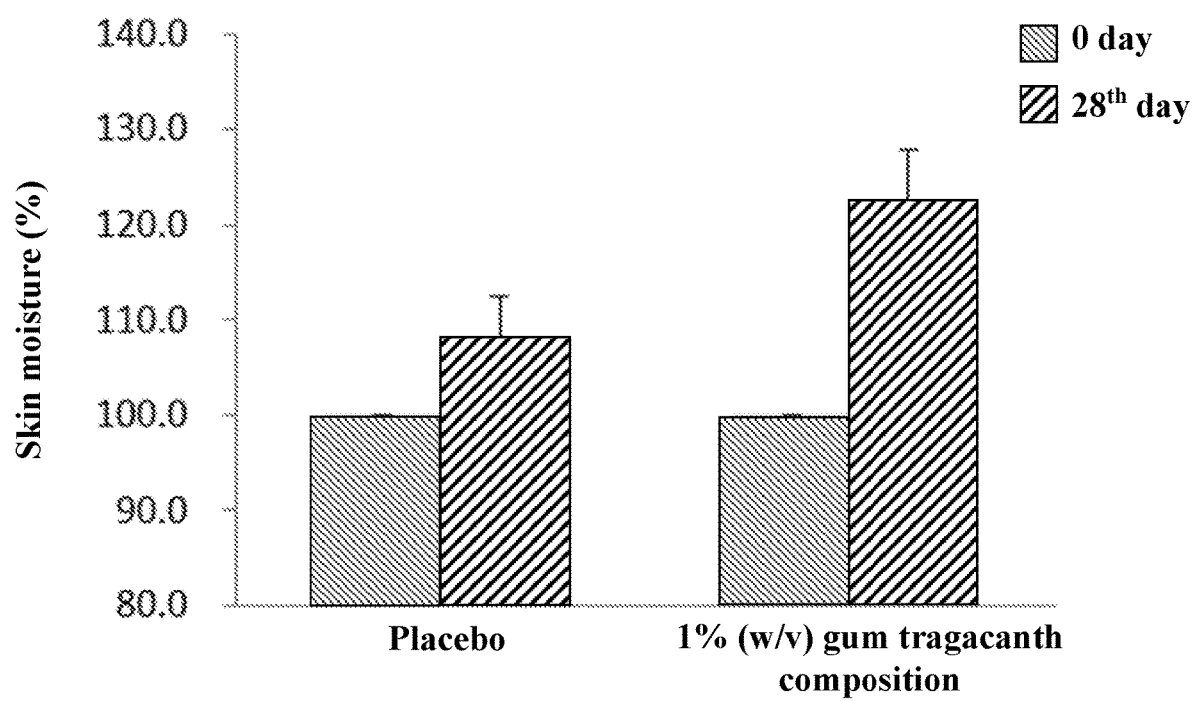
FIG. 3 shows the changes in skin moisture of the subjects, prior to and after continuously applying a 1% (w/v) gum tragacanth-containing gum tragacanth composition for 28 days, wherein the skin moisture prior to applying the composition is served as 100%.
Figure 4:
FIG. 4 shows the changes in skin brightness of the subjects, prior to and after continuously applying 1% (w/v) gum tragacanth-containing gum tragacanth composition for 28 days, wherein the skin brightness prior to applying the composition is served as 100%.

To further evaluate the effect of gum tragacanth composition on skin moisture and skin brightness, the conditions of skin moisture and skin brightness of each half side of faces of aforementioned subjects were also analyzed at the end of the $28^{th}$ day of the experiment (the conditions of skin moisture and skin brightness were also analyzed prior to the first application of 1% (w/v) gum tragacanth-containing gum tragacanth composition/placebo). The results are shown in FIGS. 3 and 4. FIG. 3 shows the changes in skin moisture of aforementioned subjects, and FIG. 4 shows the changes in skin brightness of aforementioned subjects. As shown in FIG. 3, after using 1% (w/v) gum tragacanth-containing gum tragacanth composition or the placebo continuously for 28 days in every morning and evening, the skin moisture of the subjects using placebo was improved by about 8.1%, and that of the subjects using 1% (w/v) gum tragacanth-containing gum tragacanth composition was improved by 22.7%. These results indicate that gum tragacanth composition is effective in improving skin moisture. As shown in FIG. 4, after using 1% (w/v) gum tragacanth-containing gum tragacanth composition or the placebo continuously for 28 days in every morning and evening, the skin brightness of the subjects using placebo was not significantly improved, and that of the subjects using 1% (w/v) gum tragacanth-containing gum tragacanth composition was significantly improved. These results indicate that gum tragacanth composition is effective in improving skin brightness.

Given the above, gum tragacanth composition in accordance with the present invention can effectively reduce skin sagging and improve skin moisture and brightness, and thus, can tighten skin. It is believed that the significant effect of gum tragacanth composition in reducing skin sagging is attributable to that the composition can increase the amount of elastin in the skin. Therefore, the gum tragacanth composition can be used in the manufacture of a composition for reducing skin sagging or improving skin brightness, such as a medicament, a skin care product, or a cosmetic product, which could be administered in a form of a cream, an emulsion, a dispersing liquid, a foam, a gel, a paste, a powder, a patch, or a mask and could further comprise hydroquinone, arbutin, salicylic acid, alpha hydroxy acid or a combination thereof.

BRIEF DESCRIPTION OF REFERENCE NUMERALS

Not applicable.

DEPOSIT OF BIOLOGICAL MATERIAL

Not applicable.

What is claimed is:

1. A method for treating skin sagging of a human in need thereof consisting essentially of administering via a patch a therapeutically effective amount of gum tragacanth, propanediol, and glycerol to effectively reduce the sagginess of the skin of the human in need thereof.

2. The method as claimed in claim 1, wherein the patch is topically administered to the skin of the human in need thereof at least once a day.

3. The method as claimed in claim 1, wherein the patch further consists essentially of at least one of hydroquinone, arbutin, salicylic acid, and alpha hydroxy acid.

* * * * *